US011408855B2

(12) United States Patent
Webster et al.

(10) Patent No.: US 11,408,855 B2
(45) Date of Patent: Aug. 9, 2022

(54) BULK ACOUSTIC WAVE RESONATOR WITH INCREASED DYNAMIC RANGE

(71) Applicant: QORVO US, INC., Greensboro, NC (US)

(72) Inventors: James Russell Webster, Minnetonka, MN (US); Ian Robert Harmon, Minneapolis, MN (US)

(73) Assignee: Qorvo US, Inc., Greensboro, NC (US)

( * ) Notice: Subject to any disclaimer, the term of this patent is extended or adjusted under 35 U.S.C. 154(b) by 570 days.

(21) Appl. No.: 16/503,720

(22) Filed: Jul. 5, 2019

(65) Prior Publication Data

US 2020/0011835 A1    Jan. 9, 2020

Related U.S. Application Data

(60) Provisional application No. 62/694,511, filed on Jul. 6, 2018.

(51) Int. Cl.
*G01N 29/036* (2006.01)
*G01N 29/02* (2006.01)
(Continued)

(52) U.S. Cl.
CPC ......... *G01N 29/036* (2013.01); *G01N 27/327* (2013.01); *G01N 29/022* (2013.01);
(Continued)

(58) Field of Classification Search
CPC .. G01N 29/036; G01N 27/327; G01N 29/022; G01N 33/5306; G01N 2291/0255;
(Continued)

(56) References Cited

U.S. PATENT DOCUMENTS 4,361,026 A    11/1982    Muller et al.
4,654,127 A    3/1987    Baker et al.
(Continued)

FOREIGN PATENT DOCUMENTS

CN    1 566 933 A    1/2005
CN    103403538 A    11/2013
(Continued)

OTHER PUBLICATIONS

International Search Report and Written Opinion for PCT Application No. PCT/US2019/040667 dated Oct. 7, 2019, 10 pages.
(Continued)

*Primary Examiner* — Dennis White
(74) *Attorney, Agent, or Firm* — Haynes and Boone, LLP

(57) ABSTRACT

Devices that include a low sensitivity bulk acoustic wave (BAW) resonator sensor including a surface to which a low recognition component is immobilized, the low recognition component being configured to selectively bind the analyte, an analyte molecule to which a tag is linked, or a tag, or any one of these molecules to which an amplification element-linked second recognition component is bound; a high sensitivity BAW resonator sensor including a surface to which a high recognition component is immobilized, the high recognition component being configured to selectively bind the analyte, an analyte molecule to which a tag is linked, or a tag, or any one of these molecules to which an amplification element-linked second recognition component is bound; one or more containers housing an amplification molecule, the amplification element-linked second recognition component, and optionally one or both of the tag and the analyte molecule.

18 Claims, 4 Drawing Sheets

(51) Int. Cl.
*G01N 33/53* (2006.01)
*G01N 27/327* (2006.01)

(52) U.S. Cl.
CPC . *G01N 33/5306* (2013.01); *G01N 2291/0255* (2013.01); *G01N 2291/0256* (2013.01); *G01N 2291/0426* (2013.01)

(58) Field of Classification Search
CPC ... G01N 2291/0256; G01N 2291/0426; G01N 29/222; G01N 33/54373
See application file for complete search history.

(56) References Cited

U.S. PATENT DOCUMENTS

| | | |
|---|---|---|
| 4,999,284 A | 3/1991 | Ward et al. |
| 5,404,628 A | 4/1995 | Ketcham |
| 5,405,510 A | 4/1995 | Betts et al. |
| 5,693,233 A | 12/1997 | Schembri |
| 5,821,833 A | 10/1998 | Lakin |
| 5,894,647 A | 4/1999 | Lakin |
| 5,922,591 A | 7/1999 | Anderson et al. |
| 5,932,953 A | 8/1999 | Drees et al. |
| 5,936,150 A | 8/1999 | Kobrin et al. |
| 5,942,958 A | 8/1999 | Lakin |
| 6,107,721 A | 8/2000 | Lakin |
| 6,114,635 A | 9/2000 | Lakin et al. |
| 6,235,488 B1 | 5/2001 | Tom-May et al. |
| 6,291,931 B1 | 9/2001 | Lakin |
| 6,441,703 B1 | 8/2002 | Panasik |
| 6,686,128 B1 | 2/2004 | Lakin et al. |
| 6,720,844 B1 | 4/2004 | Lakin |
| 7,241,421 B2 | 7/2007 | Webster et al. |
| 7,288,229 B2 | 10/2007 | Turner et al. |
| 7,353,695 B2 | 4/2008 | Fitch et al. |
| 7,405,054 B1 | 7/2008 | Hasenbank et al. |
| 7,419,821 B2 | 9/2008 | Davis et al. |
| 7,468,138 B2 | 12/2008 | Weinberg et al. |
| 7,666,687 B2 | 2/2010 | Webster et al. |
| 7,695,681 B2 | 4/2010 | Wang et al. |
| 7,963,151 B2 | 6/2011 | Godfrey et al. |
| 8,040,494 B2 | 10/2011 | Ermantraut et al. |
| 8,066,944 B2 | 11/2011 | Carter et al. |
| 8,084,002 B2 | 12/2011 | Carter et al. |
| 8,154,093 B2 | 4/2012 | Bradley et al. |
| 8,309,039 B2 | 11/2012 | Webster et al. |
| 8,309,364 B2 | 11/2012 | Miller et al. |
| 8,409,875 B2 | 4/2013 | Johal et al. |
| 8,467,039 B2 | 6/2013 | Ermantraut et al. |
| 9,032,782 B1 | 5/2015 | Van Deusen et al. |
| 10,234,425 B2 | 3/2019 | Salvati et al. |
| 2001/0049148 A1 | 12/2001 | Wolk et al. |
| 2004/0262162 A1 | 12/2004 | Roach et al. |
| 2005/0016276 A1 | 1/2005 | Guan et al. |
| 2006/0054941 A1 | 3/2006 | Lu et al. |
| 2006/0125489 A1 | 6/2006 | Feucht et al. |
| 2006/0133953 A1 | 6/2006 | Zhang et al. |
| 2006/0222568 A1 | 10/2006 | Wang et al. |
| 2007/0120625 A1 | 5/2007 | Larson et al. |
| 2007/0210349 A1 | 9/2007 | Lu et al. |
| 2009/0017491 A1 | 1/2009 | Lemme et al. |
| 2009/0059230 A1 | 3/2009 | Takada et al. |
| 2009/0074951 A1 | 3/2009 | Bellew et al. |
| 2009/0170119 A1 | 7/2009 | Lee et al. |
| 2009/0277271 A1 | 11/2009 | Seppa et al. |
| 2009/0282902 A1 | 11/2009 | Warthoe |
| 2010/0105079 A1 | 4/2010 | Warthoe |
| 2010/0107285 A1 | 4/2010 | Ekinci et al. |
| 2010/0127600 A1 | 5/2010 | Loschonsky et al. |
| 2010/0189601 A1 | 7/2010 | Crawford et al. |
| 2010/0218353 A1 | 9/2010 | Kolosov et al. |
| 2010/0291668 A1 | 11/2010 | Bertrand et al. |
| 2011/0008776 A1 | 1/2011 | Warthoe et al. |
| 2011/0269249 A1 | 11/2011 | Warthoe et al. |
| 2011/0316522 A1 | 12/2011 | Shinobu et al. |
| 2012/0164753 A1 | 6/2012 | Johnston et al. |
| 2012/0190128 A1 | 7/2012 | Nikbakht et al. |
| 2012/0196384 A1 | 8/2012 | Zhang et al. |
| 2012/0304776 A1 | 12/2012 | Novotny |
| 2013/0224732 A1 | 8/2013 | Lee et al. |
| 2014/0113840 A1 | 4/2014 | Margalit et al. |
| 2014/0127826 A1 | 5/2014 | Johal et al. |
| 2014/0154697 A1 | 6/2014 | Johal et al. |
| 2015/0377834 A1* | 12/2015 | Salvati ............ G01N 33/54373 435/7.92 |
| 2016/0091506 A1 | 3/2016 | Webster |
| 2017/0120242 A1 | 5/2017 | Rivas |
| 2017/0261503 A1 | 9/2017 | Murdock et al. |
| 2019/0187098 A1 | 6/2019 | Salvati et al. |

FOREIGN PATENT DOCUMENTS

| | | |
|---|---|---|
| DE | 10 2005 052752 A1 | 5/2007 |
| JP | 05-503463 A | 6/1993 |
| JP | 2012-103002 A | 5/2012 |
| WO | WO 91/05261 A1 | 4/1991 |
| WO | WO 91/10497 A1 | 7/1991 |
| WO | WO 99/00855 | 1/1999 |
| WO | WO 2004/057319 A1 | 7/2004 |
| WO | WO 2008/019693 A2 | 2/2008 |
| WO | WO 2011/102065 A1 | 8/2011 |
| WO | WO 2012/054758 A2 | 4/2012 |
| WO | WO 2014/012136 A2 | 1/2014 |
| WO | WO 2014/143680 A1 | 9/2014 |
| WO | WO 2014/190240 A1 | 11/2014 |
| WO | WO 2014/190295 A2 | 11/2014 |
| WO | WO 2016/044055 A1 | 3/2016 |
| WO | WO 2016/044132 A1 | 3/2016 |

OTHER PUBLICATIONS

U.S. Appl. No. 14/850,353, filed Sep. 10, 2015, Salvati et al.
U.S. Appl. No. 14/893,388, filed Nov. 23, 2015, Russell.
U.S. Appl. No. 16/285,304, filed Feb. 26, 2019, Salvati et al.
European Patent Application No. 14764974.3, filed Mar. 14, 2014; Extended European Search dated Oct. 10, 2016; 11 pages.
European Patent Application No. 15842191.7, filed Mar. 10, 2017; Extended European Search Report and Search Opinion dated Feb. 27, 2018; 10 pages.
European Patent Application No. 14801303.0, filed Dec. 18, 2015; Supplementary European Search Report and Search Opinion dated Nov. 22, 2016; 9 pages.
International Patent Application No. PCT/US2014/027743, filed Mar. 14, 2014; International Search Report and Written Opinion dated Jul. 10, 2014; 11 pages.
International Patent Application No. PCT/US2014/027743, filed Mar. 14, 2014; I International Preliminary Report on Patentability dated Sep. 24, 2015; 8 pages.
International Patent Application No. PCT/US2015/049387, filed Sep. 10, 2015; International Search Report and Written Opinion dated Dec. 17, 2015; 3 pages.
International Patent Application No. PCT/US2015/049387, filed Sep. 10, 2015; I International Preliminary Report on Patentability dated Mar. 21, 2017; 8 pages.
International Patent Application No. PCT/US14/39397, filed May 23, 2014; International Search Report and Written Opinion dated Oct. 2, 2014; 14 pages.
International Patent Application No. PCT/US14/39397, filed May 23, 2014; International Preliminary Report on Patentability dated Dec. 3, 2015; 11 pages.
Chen et al., "A pure shear mode ZnO film resonator for the detection of organophosphorous pesticides" Sensors and Actuators B: Chemical, Jun. 26, 2012; 171-172:1081-6.
Gan et al. "A Signal-Amplified Piezoelectric Sensor for the Detection of hs-CRP Using HRP Doped Magnetic Core-Shell $Fe_3O_4$@$SiO_2$@Au Nanostructures as Labels," 2012, *Int. J. Electrochem. Sci.*, 7:11564-77.
Kokkonen et al., "Measurement of Evanescent Wave Properties of a Bulk Acoustic Wave Resonator" IEEE Transactions on Ultrasonics, Ferroelectrics, and Frequency Control, Mar. 2012; 59(3):557-59.

(56) References Cited

OTHER PUBLICATIONS

Lee et al. "Highly sensitive biosensing using arrays of plasmonic Au nanodisks realized by nanoimprint lithography," Feb. 22, 2012, *ACS Nano*, 5(2):897-904.

Martin et al., "Optimisation of the enzyme-based determination of hydrogen peroxide using the quartz crystal microbalance," Sep. 2002, *Biosensors and Bioelectronic*, 17(9):735-39.

Patolsky et al., "Precipitation of an insoluble produce on enzyme monolayer electrodes for biosensor applications: characterization by Faradaic impedance spectroscopy, cyclic voltammetry, and microgravimetric quartz crystal microbalance analyses," Aug. 1, 1999, *Anal. Chem.*, 71(15):3171-80.

Tang et al., "Enzymatically biocatalytic precipitates amplified antibody-antigen interaction for super low level immunoassay: an investigation combined surface plasmon resonance with electrochemistry," Dec. 15, 2007, *Biosensors and Bioelectronics*, 23(5):668-74.

Waggoner et al., "Atomic Layer Deposited Silicon Dioxide Films on Nanomechanical Silicon Nitride Resonators" J Appl Phys, 2010; 107:114505. 5 pages.

Wang et al., "Label-free immunosensor based on micromachined bulk acoustic resonator for the detection of trace pesticide residues" Sensors and Actuators B: Chemical, Jan. 2014; 190:378-83. Epub Sep. 8, 2013.

Wingqvist et al., "Immunosensor utilizing a shear mode thin film bulk acoustic sensor" Sensors and Actuators B: Chemical, Oct. 20, 2007; 127(1):248-52.

Yang et al., "Effects of Diffusion Boundary Layer on Reaction Kinetics of Immunoassay in a Biosensor" J Appl Phys, Apr. 28, 2008; 10:084702. 10 pages.

Extended European Search Report dated Feb. 18, 2022 from European Application No. EP19830843.9, 9 pages.

Di Francesco F. et al, "A measurement system for odor classification based on the dynamic response of QCM sensors", IEEE Transactions On Instrumentation and Measurement, IEEE, USA, vol. 52, No. 4, Aug. 1, 2003, pp. 1079-1086, XP011101090, ISSN: 0018-9456, DOI:10.1109/TIM.2003.814826.

* cited by examiner

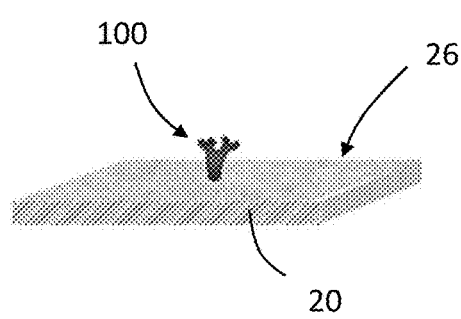
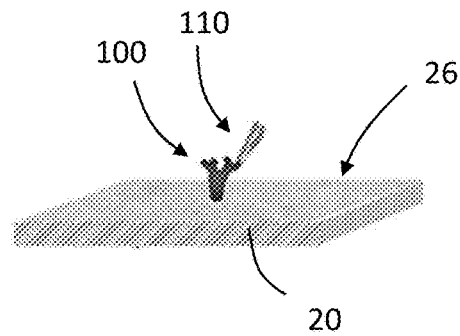
FIG. 3A  FIG. 3B
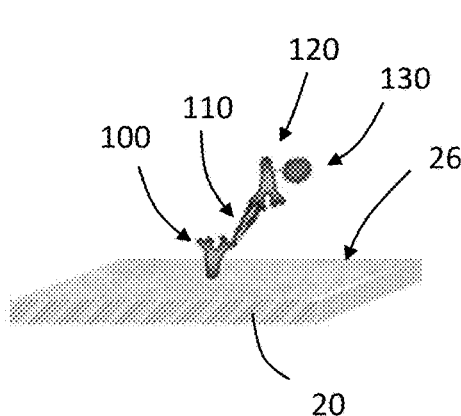
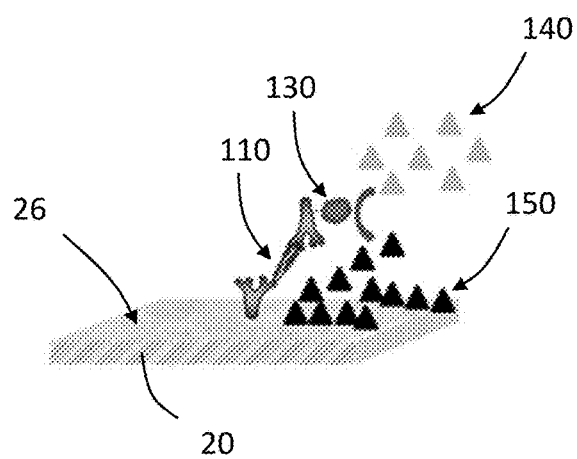
FIG. 3C  FIG. 3D

BULK ACOUSTIC WAVE RESONATOR WITH INCREASED DYNAMIC RANGE

RELATED APPLICATION

This application claims the benefit of U.S. Provisional Application No. 62/694,511, filed Jul. 6, 2018, the disclosure of which is incorporated by reference herein in its entirety.

BACKGROUND

There are numerous instruments and measurement techniques for diagnostic testing of materials related to medical, veterinary medical, environmental, biohazard, bioterrorism, agricultural commodity, and food safety. Diagnostic testing traditionally requires long response times to obtain meaningful data, involves expensive remote or cumbersome laboratory equipment, requires large sample size, utilizes multiple reagents, demands highly trained users, and can involve significant direct and indirect costs. For example, in both the human and veterinary diagnostic markets, most tests require that a sample be collected from a patient and then sent to a laboratory, where the results are not available for several hours or days. As a result, the caregiver must wait to treat the patient.

Point of use (or point of care when discussing human or veterinary medicine) solutions for diagnostic testing and analysis, although capable of solving most of the noted drawbacks, remain somewhat limited. Even some of the point of use solutions that are available are limited in sensitivity and reproducibility compared to in laboratory testing. There is also often significant direct costs to a user as there can be separate systems for each point of use test that is available.

SUMMARY

These and various other features will be apparent from a reading of the following detailed description and related drawings.

Disclosed herein are systems for detecting an analyte in a sample, the system comprising a low sensitivity bulk acoustic wave (BAW) resonator sensor comprising a surface to which a low recognition component is immobilized, the low recognition component being configured to selectively bind the analyte, an analyte molecule to which a tag is linked, or a tag, or any one of these molecules to which an amplification element-linked second recognition component is bound; a high sensitivity BAW RESONATOR sensor comprising a surface to which a high recognition component is immobilized, the high recognition component being configured to selectively bind the analyte, an analyte molecule to which a tag is linked, or a tag, or any one of these molecules to which an amplification element-linked second recognition component is bound; one or more containers housing an amplification molecule, the amplification element-linked second recognition component, and optionally one or both of the tag and the analyte molecule; a fluid path from the one or more containers to the surface of both the low and high BAW resonator sensors to which the low and high recognition components are bound; actuation circuitry configured to drive the low and high BAW resonator sensors in an oscillating motion; measurement circuitry arranged to be coupled to both the low and high BAW resonator sensors and configured to measure one or more resonator output signals representing resonance characteristics of the oscillating motion of the low and high BAW resonator sensors; and a controller operatively coupled with the actuation and measurement circuitry.

Also disclosed are kits for use with a device for detecting an analyte in a sample, the kits comprising: a system comprising: a low sensitivity bulk acoustic wave (BAW) resonator sensor comprising a surface to which a low recognition component is immobilized, the low recognition component being configured to selectively bind the analyte, an analyte molecule to which a tag is linked, or a tag, or any one of these molecules to which an amplification element-linked second recognition component is bound; a high sensitivity BAW resonator sensor comprising a surface to which a high recognition component is immobilized, the high recognition component being configured to selectively bind the analyte, an analyte molecule to which a tag is linked, or a tag, or any one of these molecules to which an amplification element-linked second recognition component is bound; and one or more containers housing an amplification molecule, the amplification element-linked second recognition component, and optionally one or both of the tag and the analyte molecule.

Also disclosed are methods for detecting an analyte in a sample, the methods comprising contacting an analyte or an analyte and a tag-linked analyte molecule, a low recognition component, and an amplification element-linked second recognition component to generate a complex comprising the low recognition component and the amplification element-linked second recognition component, wherein the low recognition component is immobilized relative to a surface of a low BAW resonator sensor and is configured to selectively bind one or more of the analyte, the analyte molecule to which the tag is linked or the tag, or any one or more of these molecules bound to the second recognition component; contacting an analyte or an analyte and a tag-linked analyte molecule, a high recognition component, and an amplification element-linked second recognition component to generate a complex comprising the high recognition component and the amplification element-linked second recognition component, wherein the high recognition component is immobilized relative to a surface of a high BAW resonator sensor and is configured to selectively bind one or more of the analyte, the analyte molecule to which the tag is linked or the tag, or any one or more of these molecules bound to the second recognition component; wherein the amplification element-linked second recognition component is configured to selectively bind the analyte, the analyte molecule to which the tag is linked or the tag, or any one or more of these molecules bound to the low and high recognition components; wherein the low recognition component and the high recognition components have different affinity for the analyte molecule; contacting the linked amplification element with an amplification precursor under conditions to convert the amplification precursor into a molecule that adds mass at a surface of the BAW resonator; and measuring mass added at the surface of the BAW resonator.

Also disclosed are methods for detecting an analyte in a sample, the method comprising contacting an analyte or an analyte and a tag-linked analyte molecule, a low recognition component, and an amplification element-linked second recognition component to generate a complex comprising the low recognition component and the amplification element-linked second recognition component, wherein the low recognition component is immobilized relative to a surface of a low BAW resonator sensor, is configured to selectively bind one or more of the analyte, the analyte molecule to which the tag is linked or the tag, or any one or more of these molecules bound to the second recognition component and has a low concentration on the surface to which it is immobilized; contacting an analyte or an analyte and a tag-linked analyte molecule, a high recognition component, and an amplification element-linked second recognition component to generate a complex comprising the high recognition component and the amplification element-linked second recognition component, wherein the high recognition component is immobilized relative to a surface of a high BAW resonator, is configured to selectively bind one or more of the analyte, the analyte molecule to which the tag is linked or the tag, or any one or more of these molecules bound to the second recognition component and has a high concentration on the surface to which it is immobilized; wherein the amplification element-linked second recognition component is configured to selectively bind the analyte, the analyte molecule to which the tag is linked or the tag, or any one or more of these molecules bound to the low and high recognition components; wherein the low concentration of the first recognition component is lower than the high concentration of the second recognition component; contacting the linked amplification element with an amplification precursor under conditions to convert the amplification precursor into a molecule that adds mass at a surface of the BAW resonator; and measuring mass added at the surface of the BAW resonator.

BRIEF DESCRIPTION OF THE DRAWINGS

FIGS. 3A-D are schematic drawings illustrating an embodiment of signal amplification on a surface of a bulk acoustic wave (BAW) resonator sensor.

Figure 1A:
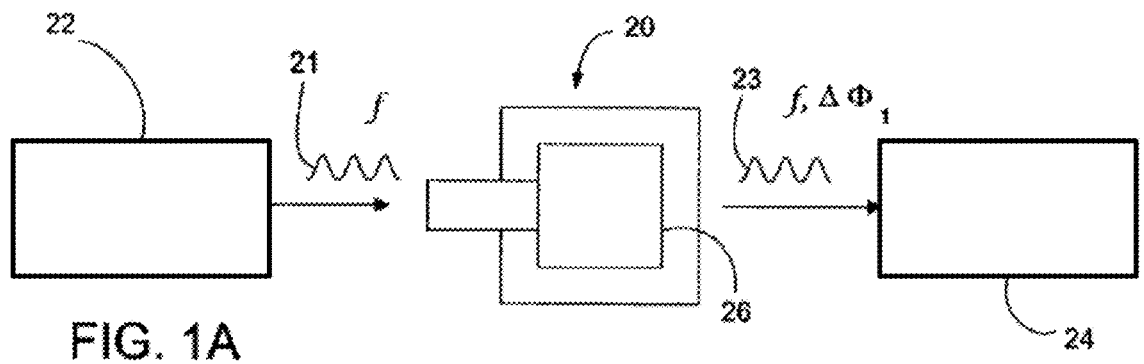
FIGS. 1A-1C are schematic diagrams illustrating the operational principles of embodiments of bulk acoustic wave (BAW) resonator sensing devices.

The schematic drawings are not necessarily to scale. Like numbers used in the figures refer to like components, steps and the like. However, it will be understood that the use of a number to refer to a component in a given figure is not intended to limit the component in another figure labeled with the same number. In addition, the use of different numbers to refer to components is not intended to indicate that the different numbered components cannot be the same or similar.

DETAILED DESCRIPTION

In the following detailed description several specific embodiments of compounds, compositions, products and methods are disclosed. It is to be understood that other embodiments are contemplated and may be made without departing from the scope or spirit of the present disclosure. The following detailed description, therefore, is not to be taken in a limiting sense.

All scientific and technical terms used herein have meanings commonly used in the art unless otherwise specified. The definitions provided herein are to facilitate understanding of certain terms used frequently herein and are not meant to limit the scope of the present disclosure.

As used in this specification and the appended claims, the singular forms "a", "an", and "the" encompass embodiments having plural referents, unless the content clearly dictates otherwise.

As used in this specification and the appended claims, the term "or" is generally employed in its sense including "and/or" unless the content clearly dictates otherwise. The term "and/or" means one or all of the listed elements or a combination of any two or more of the listed elements.

As used herein, "have", "having", "include", "including", "comprise", "comprising" or the like are used in their open ended sense, and generally mean "including, but not limited to". It will be understood that "consisting essentially of", "consisting of", and the like are subsumed in "comprising" and the like. As used herein, "consisting essentially of," as it relates to a composition, product, method or the like, means that the components of the composition, product, method or the like are limited to the enumerated components and any other components that do not materially affect the basic and novel characteristic(s) of the composition, product, method or the like.

The words "preferred" and "preferably" refer to embodiments of the invention that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the disclosure, including the claims.

Also herein, the recitations of numerical ranges by endpoints include all numbers subsumed within that range (e.g., 1 to 5 includes 1, 1.5, 2, 2.75, 3, 3.80, 4, 5, etc. or 10 or less includes 10, 9.4, 7.6, 5, 4.3, 2.9, 1.62, 0.3, etc.). Where a range of values is "up to" a particular value, that value is included within the range.

Any direction referred to herein, such as "top," "bottom," "left," "right," "upper," "lower," and other directions and orientations are described herein for clarity in reference to the figures and are not to be limiting of an actual device or system or use of the device or system. Devices or systems as described herein may be used in a number of directions and orientations.

Disclosed devices advantageously combine high sensitivity with a large dynamic range. The sensitivity of disclosed devices can be enhanced through a number of protocols. One of which is disclosed in U.S. patent application Ser. No. 16/285,304 entitled "THIN FILM BULK ACOUSTIC RESONATOR WITH SIGNAL ENHANCEMENT", filed on Feb. 26, 2019 and published as United States Patent Publication Number 2019/0187098, the disclosure of which is incorporated herein by reference thereto.

Sensors, Devices and Systems

The sensors disclosed herein include at least two thin film resonator sensor, such as bulk acoustic wave (BAW) resonator sensors. In disclosed devices the at least two BAW resonator sensors have different sensitivities to the analyte of interest. One sensor can be referred to as the high sensitivity sensor and the other sensor can be referred to as the low sensitivity sensor. It is noted that this terminology is only meant to convey relative sensitivity of the two sensors and does not indicate the sensitivity of the two sensors to any external sensor or device.

A BAW resonator sensor includes a piezoelectric layer, or piezoelectric substrate, and input and output transducer. BAW resonator sensors are small sensors making the technology suitable for use in handheld devices. Accordingly, a handheld device for detecting target analytes comprising a sensor described herein is contemplated.

Figure 1B:
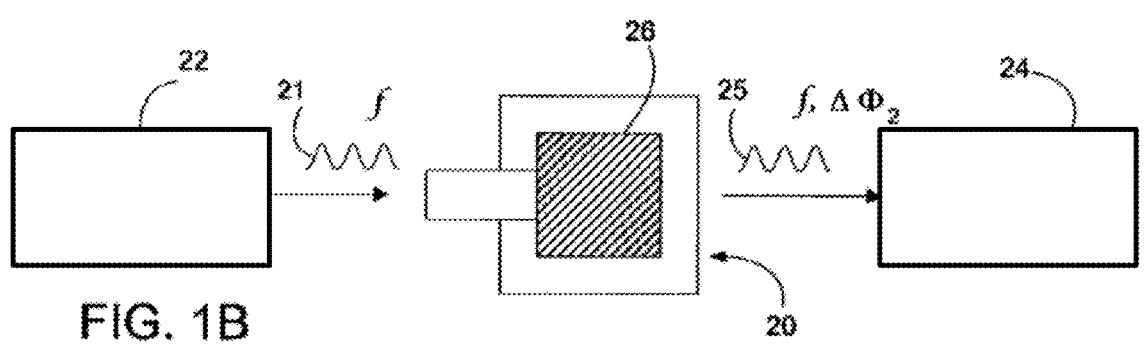

Turning now to the drawings with reference to FIGS. 1A and 1B, general operating principles of an embodiment of a bulk-acoustic wave piezoelectric resonator 20 used as a sensor to detect an analyte are shown. The resonator 20 typically includes a planar layer of piezoelectric material bounded on opposite sides by two respective metal layers which form the electrodes of the resonator. The two surfaces of the resonator are free to undergo vibrational movement when the resonator is driven by a signal within the resonance band of the resonator. When the resonator is used as a sensor, at least one of its surfaces is adapted to provide binding sites for the material being detected. The binding of the material on the surface of the resonator alters the resonant characteristics of the resonator, and the changes in the resonant characteristics are detected and interpreted to provide quantitative information regarding the material being detected.

By way of example, such quantitative information may be obtained by detecting a change in the insertion or reflection coefficient phase shift of the resonator caused by the binding of the material being detected on the surface of the resonator. Such sensors differ from those that operate the resonator as an oscillator and monitor changes in the oscillation frequency. Rather such sensors insert the resonator in the path of a signal of a pre-selected frequency and monitor the variation of the insertion or reflection coefficient phase shift caused by the binding of the material being detected on the resonator surface. Of course, sensors that monitor changes in oscillation frequency may also be employed in accordance with signal amplification described herein.

In more detail, FIG. 1A shows the resonator 20 before the material being detected is bound to its surface 26. The depicted resonator 20 is electrically coupled to a signal source 22, which provides an input electrical signal 21 having a frequency f within the resonance band of the resonator. The input electrical signal is coupled to the resonator 20 and transmitted through the resonator to provide an output electrical signal 23. In the depicted embodiment, the output electrical signal 23 is at the same frequency as the input signal 21, but differs in phase from the input signal by a phase shift $\Delta\Phi_1$, which depends on the piezoelectric properties and physical dimensions of the resonator. The output signal 23 is coupled to a phase detector 24 which provides a phase signal related to the insertion phase shift.

FIG. 1B shows the sensing resonator 20 with the material being detected bound on its surface 26. The same input signal is coupled to the resonator 20. Because the resonant characteristics of the resonator are altered by the binding of the material as a perturbation, the insertion phase shift of the output signal 25 is changed to $\Delta\Phi_2$. The change in insertion phase shift caused by the binding of the material is detected by the phase detector 24. The measured phase shift change is related to the amount of the material bound on the surface of the resonator.

Figure 1C:
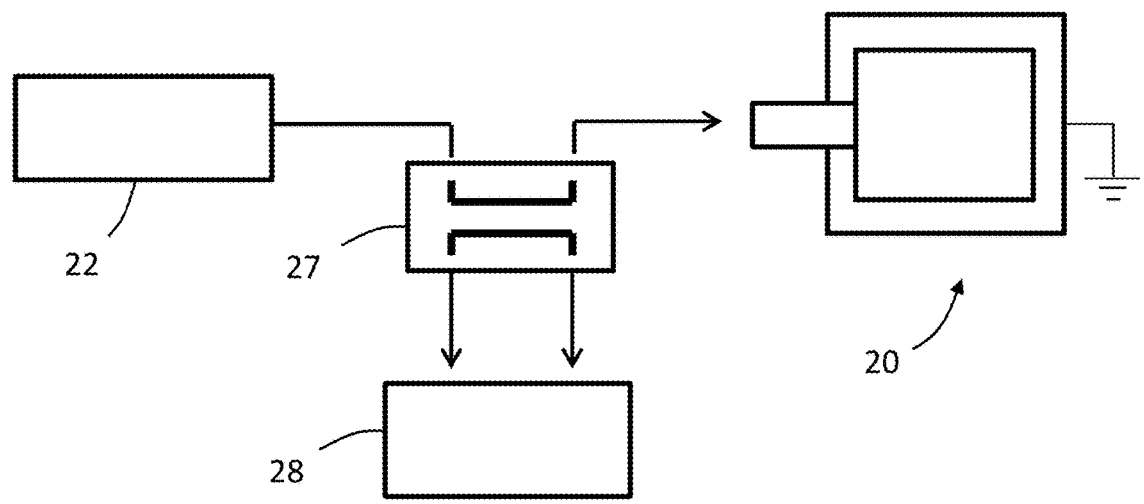

FIG. 1C shows an alternative to measuring the insertion phase of the resonator. A directional coupler 27 is added between the signal source 22 and the resonator 20 with the opposite electrode grounded. A phase detector 28 is configured to measure the phase shift of the reflection coefficient as a result of material binding to the resonator surface.

Other BAW resonator phase-shift sensors that may be employed with the signal amplification aspects described herein include those described in, for example, U.S. Pat. No. 8,409,875, which patent is hereby incorporated herein by reference in its entirety to the extent that it does not conflict with the disclosure presented herein. For example, sensor apparatuses may include (i) a sensing resonator comprising binding sites for an analyte; (ii) actuation circuitry configured to drive the sensing resonator in an oscillating motion; (iii) measurement circuitry arranged to be coupled to the sensing resonator and configured to measure one or more resonator output signals representing resonance characteristics of the oscillating motion of the sensing resonator; and (iv) a controller operatively coupled with the actuation and measurement circuitry. The controller can be interfaced with data storage containing instructions that, when executed, cause the controller to adjust the frequency at which the actuation circuitry drives the sensing resonator to maintain a resonance point of the sensing resonator. Accordingly, sensing may be accomplished by actuating the BAW resonator into an oscillating motion; measuring one or more resonator output signals representing resonance characteristics of the oscillating motion of the BAW resonator; and adjusting the actuation frequency of the sensing resonator to maintain a resonance point of the BAW resonator. In embodiments, the frequency at which the actuation circuitry drives the sensing resonator is a frequency of maximum group delay.

Such phase detection approaches can be advantageously used with piezoelectric resonators of different resonant frequencies.

In various embodiments, BAW resonators for use with the methods, devices, and system described herein have resonance frequencies of about 500 MHz or greater, such as about 700 MHz or greater, about 900 MHz or greater, about 1 MHz or greater, 1.5 GHz or greater, about 1.8 GH or greater, about 2 GHz or greater, 2.2 GHz or greater, 2.5 GHz or greater, about 3 GHZ or greater, or about 5 GHZ or greater can provide enhanced sensitivity when used with amplification element mediated mass loaded, which is described in more detail below. In embodiments, the BAW resonators have resonance frequencies of from about 500 MHz to about 5 GHz, such as from about 900 MHz to about 3 GHz, or from about 1.5 GHz to about 2.5 GHz. Some of such frequencies are substantially higher than frequencies of previously described piezoelectric resonators.

The sensing resonators described herein are thin-film resonators (TFR). Thin film resonators comprise a thin layer of piezoelectric material deposited on a substrate, rather than using, for example, AT-cut quartz. The piezoelectric films typically have a thickness of less than about 5 micrometers, such as less than about 2 micrometers, and may have thicknesses of less than about 100 nanometers. Thin-film resonators are generally preferred because of their high resonance frequencies and the theoretically higher sensitivities. Depending on the applications, a thin-film resonator used as the sensing element may be formed to support either longitudinal or shear bulk-acoustic wave resonant modes. Preferably, the sensing element is formed to support shear bulk-acoustic wave resonant modes, as they are more suitable for use in a liquid sample.

Additional details regarding sensor devices and systems that may employ TFRs are described in, for example, U.S. Pat. No. 5,932,953 issued Aug. 3, 1999 to Drees et al., which patent is hereby incorporated herein by reference in its entirety to the extent that it does not conflict with the disclosure presented herein.

TFR sensors may be made in any suitable manner and of any suitable material. By way of example, a resonator may include a substrate such as a silicon wafer or sapphire, a Bragg mirror layer or other suitable acoustic isolation means, a bottom electrode, a piezoelectric material, and a top electrode.

Any suitable piezoelectric material may be used in a TFR. Examples of suitable piezoelectric substrates include lithium tantalate (LiTaO$_3$), lithium niobate (LiNbO$_3$), Zinc Oxide (ZnO), aluminum nitride (AlN), plumbum zirconate titanate (PZT) and the like.

Electrodes may be formed of any suitable material, such as aluminum, tungsten, gold, titanium, molybdenum, or the like. Electrodes may be deposited by vapor deposition or may be formed by any other suitable process.

Any suitable device or system may employ a thin film resonator and amplification as described herein. By way of example and with reference to FIG. 2, a system for detecting an analyte may include a container 10 (or more than one container), the thin film resonator 20, actuation circuitry 22, measurement circuitry 29, and control electronics 30. A fluid path couples the one or more containers 10 to the resonator 20. The control electronics 30 are operably coupled to the actuation circuitry and the measurement circuitry. In embodiments, control electronics 30 are configured to modify the frequency at which the actuation circuitry 22 oscillates the resonator 20 based on input from the measurement circuitry 29.

Figure 2:
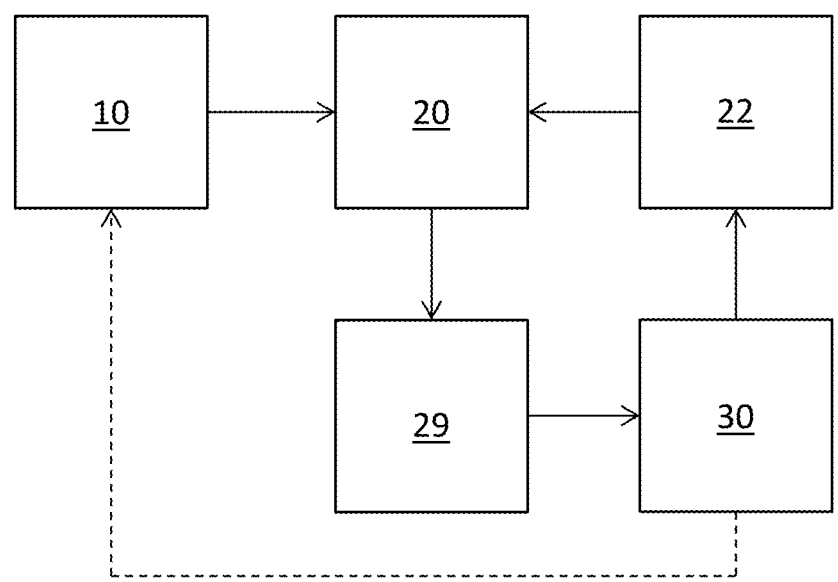
FIG. 2 is a schematic diagram showing components of a BAW resonator system for detecting an analyte.

Still with reference to FIG. 2, the container 10 (or more than one container) may house an amplification molecule, an amplification element-linked second recognition component or components thereof, and optionally one or more of a tag, an analyte molecule, and a first recognition component. Each of these reagents is described in more detail below. Control electronics 30 may control the flow of such reagents from container 10 to resonator 20; e.g. via a pump, vacuum, or the like.

Any suitable control electronics 30 may be employed. For example, control electronics may include a processor, controller, memory, or the like. Memory may include computer-readable instructions that, when executed by processor or controller cause the device and control electronics to perform various functions attributed to device and control electronics described herein. Memory may include any volatile, non-volatile, magnetic, optical, or electrical media, such as a random access memory (RAM), read-only memory (ROM), non-volatile RAM (NVRAM), electrically-erasable programmable ROM (EEPROM), flash memory, or any other digital media. Control electronics 30 may include any one or more of a microprocessor, a controller, a digital signal processor (DSP), an application specific integrated circuit (ASIC), a field-programmable gate array (FPGA), or equivalent discrete or integrated logic circuitry. In some examples, control electronics 30 may include multiple components, such as any combination of one or more microprocessors, one or more controllers, one or more DSPs, one or more ASICs, or one or more FPGAs, as well as other discrete or integrated logic circuitry. The functions attributed to control electronics herein may be embodied as software, firmware, hardware or any combination thereof.

Molecular Recognition and Signal Amplification

Molecular recognition of a sample comprising a significant background signal may be facilitated by amplification of the signal. The sensors, systems and methods described herein employ a second recognition component comprising an amplification element such as a linked enzyme.

The BAW resonator sensors, at the higher frequency ranges described herein, responded very efficiently to mass increase of the sensor surface due to precipitation of a substrate cleaved by an enzyme.

Referring now to FIGS. 3A-D, schematic drawings illustration enzyme amplification on a BAW resonator are shown. As depicted in FIG. 3A, a molecular recognition component 100 configured to bind to an analyte is immobilized on a surface 26 of a resonator 20. The resonator 20 having immobilized molecular recognition component 100 may be contacted with a composition comprising an analyte 110, which may bind molecular recognition component 100 (see FIG. 3B). The resonator 20 having immobilized molecular recognition component 100 to which analyte 110 is bound may be contacted with a composition comprising a second molecular recognition component 120 linked to an amplification element 130 such as an enzyme. The second molecular recognition component 120 is configured to bind to analyte 110 such that the second molecular recognition component 120 and linked amplification element 130 are immobilized relative to the surface 26 (see FIG. 3C). In the depicted embodiments, a soluble substrate 140 may be converted by amplification element 130 to an insoluble product 150, which precipitates and accumulates on the surface 26 of the sensor 20, thereby amplifying the mass signal as a function of amount or concentration of bound analyte 110 (see FIG. 3D).

It will be understood that the series of events depicted in FIGS. 3A-3D are shown for purposes of illustration and that any other suitable sequence of events may be employed. For example, the analyte 110 may be contacted with the second molecular recognition component 120 (and bound amplification element 130) before the analyte (with bound second molecular recognition component) is contacted to the surface 26 of the resonator 20 relative to which the molecular recognition component 100 is immobilized. The substrate 140 may be present at the time the second molecular recognition component 120—amplification element 130 is added or may be added later. In any case, washing may be performed prior to amplification.

Non-limiting examples of target analytes include nucleic acids, proteins, peptides, antibodies, enzymes, carbohydrates, chemical compounds, or infectious species such as bacteria, fungi, protozoa, viruses and the like. In certain applications, the target analyte is capable of binding more than one molecular recognition component.

Any suitable molecular recognition component (e.g., 100 in FIG. 3) may be bound to the surface of a resonator. The molecular recognition component preferably selectively binds to the analyte of interest. By way of example, the molecular recognition component may be selected from the group consisting of nucleic acids, nucleotide, nucleoside, nucleic acids analogues such as PNA and LNA molecules, proteins, peptides, antibodies including IgA, IgG, IgM, IgE, lectins, enzymes, enzymes cofactors, enzyme substrates, enzymes inhibitors, receptors, ligands, kinases, Protein A, Poly U, Poly A, Poly lysine, triazine dye, boronic acid, thiol, heparin, polysaccharides, coomassie blue, azure A, metal-binding peptides, sugar, carbohydrate, chelating agents, prokaryotic cells and eukaryotic cells.

Any suitable method for immobilizing a molecular recognition component on a surface of a BAW resonator may be used. By way of example, a uniform coating of epoxy silane may be deposited on the sensor surface using a vapor deposition process. Test and reference molecular recognition components, such as antibodies, may then be deposited onto the test and reference resonators using, for example, piezo based nanodispensing technology. Primary amines on the antibodies react with the epoxide groups covalently binding the antibody to the sensor surface. By way of further example, a thiol group, if present, of the molecular recognition component bind to a surface of the BAW RESONATOR. The surface of the BAW RESONATOR may be modified, as appropriate or necessary, to permit binding of the molecular recognition component.

Any suitable molecular recognition components, such as those described above, may be used as the second molecular recognition component (e.g., 120 in FIG. 3). The second molecular recognition component may be linked to any suitable amplification element, such as an enzyme. Preferably, the second molecular recognition component is an antibody and the amplification element is an enzyme.

Any suitable amplification element may be linked to the second molecular recognition component. In embodiments, the amplification element is an activatable polymerization initiator, such as a photoinitiator, a chemical initiator, or a thermoinitiator. The polymerization initiator may be activated in the presence of one or more monomers to cause a polymer to graft from the second molecular recognition component. In embodiments, the amplification element is an enzyme. In embodiments, the enzyme is capable of converting a substrate that is soluble in the assay environment to an insoluble product that precipitates on the surface of the sensor. Examples of suitable enzymes include alkaline phosphatase (ALP), horse radish peroxidase (HRP), beta galactosidase, and glucose oxidase.

Examples of enzyme/substrate systems that are capable of producing an insoluble product which is capable of accumulating on a surface of a BAW resonator include alkaline phosphatase and 5-bromo-4-chloro-3-indolylphosphate/nitro-blue tetrazolium chloride (BCIP/NBT). The enzymatically catalyzed hydrolysis of BCIP produces an insoluble dimer, which may precipitate on the surface of the sensors. Other analogous substrates having the phosphate moiety replaced with such hydrolytically cleavable functionalities as galactose, glucose, fatty acids, fatty acid esters and amino acids can be used with their complementary enzymes. Other enzyme/substrate systems include peroxidase enzymes, for example horse radish peroxidase (HRP) or myeloperoxidase, and one of the following: benzidene, benzidene dihydrochloride, diaminobenzidene, o-tolidene, o-dianisidine and tetramethyl-benzidene, carbazoles, particularly 3-amino-9-ethylcarbazole, and various phenolic compounds all of which have been reported to form precipitates upon reaction with peroxidases. Also, oxidases such as alphahydroxy acid oxidase, aldehyde oxidase, glucose oxidase, L-amino acid oxidase and xanthine oxidase can be used with oxidizable substrate systems such as a phenazine methosulfate-nitriblue tetrazolium mixture.

It will be understood that any type of competition assay may be employed. It will be further understood that the analyte may be modified to include a tag recognizable by the first or second recognition complex, such as a streptavidin tag; biotin tag; a chitin binding protein tag; a maltose binding protein tag; a glutathione-S-transferase tag; a poly (His) tag; an epitope tag such as a Myc tag, a HA tag, or a V5 tag; or the like. It will be further understood that the tag-linked analyte may include a variant or derivative of the analyte. The variant or derivative is a variant or derivative that is selectively recognizable by the first or second molecular recognition component that is configured to recognize the analyte. In some situations, it may be desirable that the variant or derivative analyte have an affinity for the first or second molecular recognition component that is different than the affinity of the non-tag-linked analyte. The variant or derivative of the analyte may be a variant or derivative that allows for ease of manufacture of the tag-linked analyte. For example, the tag-linked analyte may comprise a recombinant polypeptide, etc.

When competition assays employing tag-linked analyte molecules are performed, the tag-linked analyte molecule, rather than or in addition to the analyte, may bind a first molecular recognition component immobilized on a surface of a resonator.

In disclosed devices the at least two BAW resonator sensors have different sensitivities to the analyte of interest: the high sensitivity sensor and the low sensitivity sensor. The sensitivity of the low sensitivity sensor can be tailored with respect to the high sensitivity sensor by immobilizing on the low sensitivity sensor a molecular recognition component with a lower affinity, a molecular recognition component with a lower capacity, or a combination thereof than is present on the high sensitivity sensor. This can of course also be explained with respect to the high sensitivity sensor, which would have immobilized thereon a molecular recognition component with a higher affinity, a molecular recognition component with a higher capacity or a combination thereof than is present on the low sensitivity sensor. The affinity, capacity, or both of the molecular recognition component can be tailored by modifying the coating (amount, concentration, etc.) of the same molecular recognition component, using a different molecular recognition component, or a combination thereof.

In some embodiments, where the coating is modified various parameters can be utilized to affect the relative sensitivities, including for example the concentration of the molecular recognition component in the coating for example. In some embodiments, a filler molecule, which could also be referred to as a non-specific component can be mixed in the coating composition along with the molecular recognition component. The relative amounts of the non-specific component and the molecular recognition component can then be chosen to determine the sensitivity level of the low sensitivity sensor.

In some embodiments, different molecular recognition components can be utilized to affect the relative sensitivities. For example, molecular recognition components with different sensitivities to the analyte of interest can be included on the two sensors. For example, a molecular recognition component with a lower affinity for the analyte of interest than that on the high sensitivity sensor can be coated on the low sensitivity sensor and a molecular recognition component with a higher affinity than that on the low sensitivity sensor can be coated on the high sensitivity sensor.

The devices, systems, and methods described herein may be employed to detect a target analyte in a sample. The devices may find use in numerous chemical, environmental, food safety, or medial applications. By way of example, a sample to be tested may be, or may be derived from blood, serum, plasma, cerebrospinal fluid, saliva, urine, and the like. Other test compositions that are not fluid compositions may be dissolved or suspended in an appropriate solution or solvent for analysis.

Non-limiting examples of target analytes include nucleic acids, proteins, peptides, antibodies, enzymes, carbohydrates, chemical compounds, or infectious species such as bacteria, fungi, protozoa, viruses, pesticides and the like. In certain applications, the target analyte is capable of binding more than one molecular recognition component.

The present disclosure is illustrated by the following examples. It is to be understood that the particular examples, assumptions, modeling, and procedures are to be interpreted broadly in accordance with the scope and spirit of the disclosure as set forth herein.

Device for Detecting Thyroid Stimulating Hormone (TSH)

Table 1 shows the dynamic range of a few central-lab based human TSH tests currently available. Normal range levels for children and adults have been shown to be 0.27-4.2 uIU/ml (95th percentile) (Roche Elecsys TSH Factsheet).

TABLE 1

Measurement ranges of a few central-lab TSH tests. Only Access TSH (3rd IS) is based on the 3rd WHO reference TSH preparation. All others are based on the 2nd WHO reference TSH preparation. 6.8 IU/ng conversion is based on the scripps TSH antigen used to make the BAW sensor assay measurements.

|  | Measuring range (uIU/ml) | Approximate range (pg/ml) (6.8 IU/mg) |
|---|---|---|
| Roche Elecsys TSH | 0.005-100 | 0.735-14705 |
| Beckman Coulter Access TSH ($3^{rd}$ IS) | 0.005-50 | 0.735-7353 |
| Beckman Coulter Access HYPERsensitive hTSH | 0.015-100 | 2.21-14705 |
| Beckman Coulter Access Fast hTSH | 0.030-100 | 4.41-14705 |

Figure 4:
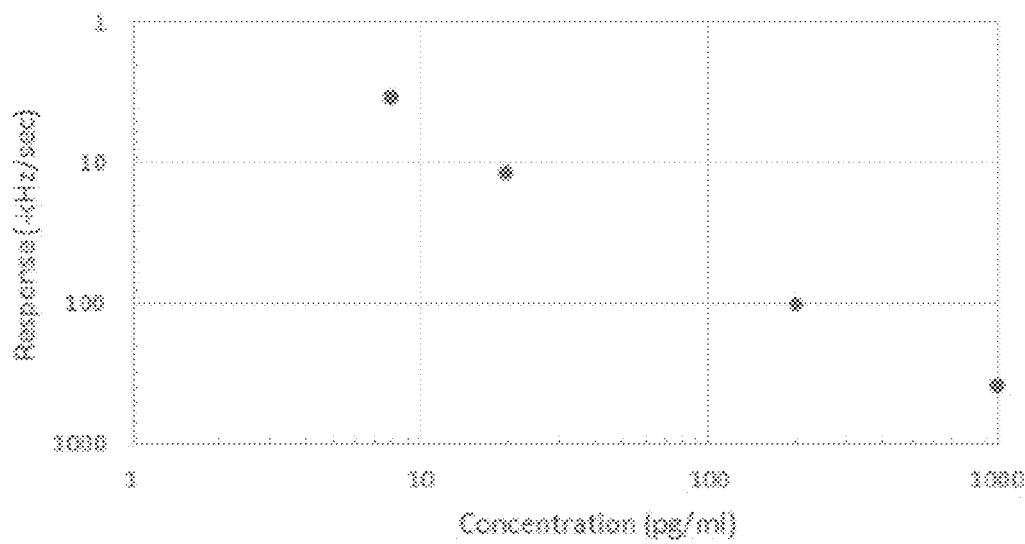
FIG. 4 is a calibration curve of a BAW resonator sensor immunoassay for human TSH.

FIG. 4 shows a calibration curve of a BAW sensor immunoassay for human TSH. At the upper limit the 1000 pg/ml the frequency is shifting over 350 kHz/sec. At higher concentrations the rapid shift of the BAW sensor becomes difficult to track and the precipitate significantly dampens the resonator. In order to compare with the dynamic range of the Access TSH (3rd IS) a 7 fold increase in dynamic range is needed. While some improvements can be made with improved electronics and software algorithms, this may only amount to a 2 fold increase.

Figure 5:
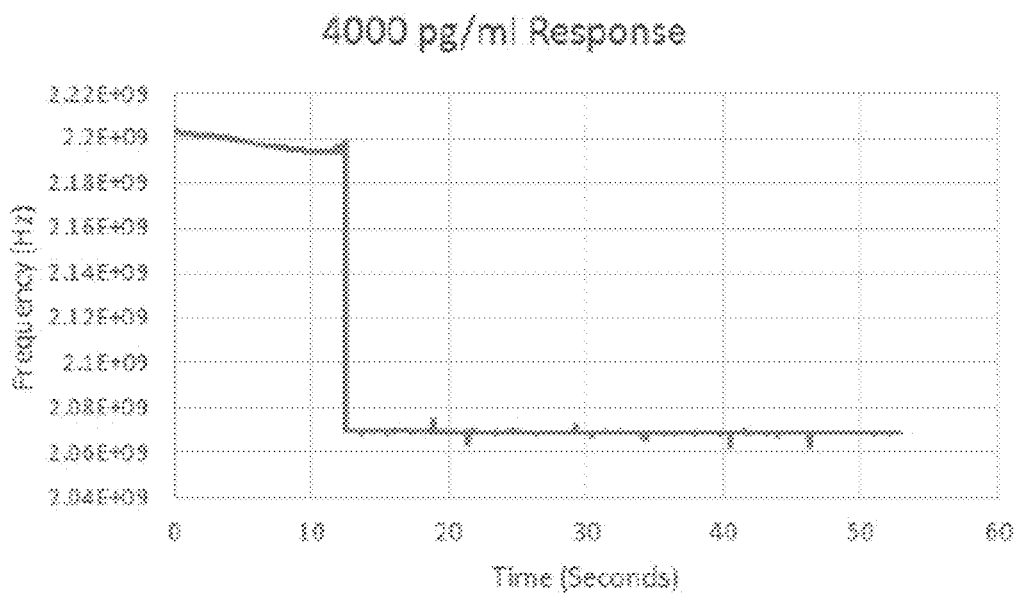
FIG. 5 is a curve plotting results obtained at high concentrations employing a system generally as described in U.S. 2015/0377834 A1, the disclosure of which is incorporated herein by reference thereto.

FIG. 5 shows that at high concentrations the tracking algorithm is unable to track the high level of frequency shift employing a system generally as described in U.S. 2015/0377834 A1. Frequency tracking is lost at about 12 seconds. Even if the first 10 seconds are fit, a large amount of variability is observed from part to part due to the large signals and extreme dampening of the resonators.

By incorporating two resonators, the dynamic range of the BAW immunoassay may be increased. The first resonator is a high sensitivity resonator capable of generating a response similar to that shown in FIG. 4. The second resonator is a lower sensitivity resonator capable of measuring at higher concentration levels without saturating the measurement system. The second resonator is made lower in sensitivity by immobilizing a mixture of specific capture ligand and non-specific filler molecule at a fixed ratio such as 1:4 (or any other suitable ratio). This is effective because, in the enzyme enhanced BAW system, the limit in the dynamic range is not the immunoassay itself, but the ability of the system to track the rapidly shifting resonators. In many cases the immunoassay binds much less than 10% of the total surface capacity. Therefore, when immobilizing a 1:4 mixture of specific to non-specific capture molecules, the resultant signal produced from the resonator should be scaled by the mixture ratio, and therefore increase the dynamic range by the same ratio. When the concentrations exceed the dynamic range of the high sensitivity resonator, the instrument then uses the lower sensitivity resonator to report the concentration value. For intermediate concentrations both resonators could be used to improve precision of the result.

As an alternative to mixing, the lower sensitivity resonator can be prepared using a lower affinity antibody. This would effectively reduce the sensitivity by the ratio of the antibody affinities and thereby increase the dynamic range similarly.

Thus, embodiments of BULK ACOUSTIC WAVE RESONATOR WITH INCREASED DYNAMIC RANGE are disclosed. The implementations described above and other implementations are within the scope of the following claims. One skilled in the art will appreciate that the present disclosure can be practiced with embodiments other than those disclosed. The disclosed embodiments are presented for purposes of illustration and not limitation.

What is claimed is:

1. A system for detecting an analyte in a sample, comprising:
    a low sensitivity bulk acoustic wave (BAW) resonator sensor comprising a surface to which a low recognition component is immobilized,
        the low recognition component being configured to selectively bind the analyte, an analyte molecule to which a tag is linked, or a tag, or any one of these molecules to which an amplification element-linked second recognition component is bound;
    a high sensitivity BAW resonator sensor comprising a surface to which a high recognition component is immobilized,
        the high recognition component being configured to selectively bind the analyte, an analyte molecule to which a tag is linked, or a tag, or any one of these molecules to which an amplification element-linked second recognition component is bound;
    one or more containers housing an amplification molecule, the amplification element-linked second recognition component, and optionally one or both of the tag and the analyte molecule;
    a fluid path from the one or more containers to the surface of both the low and high sensitivity BAW resonator sensors to which the low and high recognition components are bound;
    actuation circuitry configured to drive the low and high BAW sensitivity resonator sensors in an oscillating motion;
    measurement circuitry arranged to be coupled to both the low and high sensitivity BAW resonator sensors and configured to measure one or more resonator output signals representing resonance characteristics of the oscillating motion of the low and high sensitivity BAW resonator sensors; and
    a controller operatively coupled with the actuation circuitry and the measurement circuitry.

2. The system of claim 1, wherein the low and high recognition components are different.

3. The system of claim 2, wherein the low recognition component has a lower affinity for the analyte molecule than does the high recognition component.

4. The system of claim 1, wherein the low and high recognition components are the same and a concentration of the low recognition component on the surface of the low sensitivity BAW resonator sensor is different from a concentration of the high recognition component on the surface of the high sensitivity BAW resonator sensor.

5. The system of claim 4, wherein the concentration of the low recognition component on the surface of the low sensitivity BAW resonator sensor is lower than the concentration of the high recognition component on the surface of the sensitivity high sensitivity BAW resonator sensor.

6. The system of claim 4, wherein the surface of at least the low sensitivity BAW resonator sensor also has a non-specific component immobilized thereon.

7. The system of claim 1, wherein the controller utilizes the output signal from the low sensitivity BAW resonator sensor, the high sensitivity BAW resonator sensor, or both.

8. The system of claim 1, wherein the controller utilizes the output signal from the low sensitivity BAW resonator sensor, or the high sensitivity BAW resonator sensor, but not both.

9. The system of claim 1, wherein the controller utilizes both the output signal from the low sensitivity BAW resonator sensor and the high sensitivity BAW resonator sensor.

10. A kit for use with a device for detecting an analyte in a sample, comprising:
   a system comprising:
   a low sensitivity bulk acoustic wave (BAW) resonator sensor comprising a surface to which a low recognition component is immobilized,
     the low recognition component being configured to selectively bind the analyte, an analyte molecule to which a tag is linked, or a tag, or any one of these molecules to which an amplification element-linked second recognition component is bound;
   a high sensitivity BAW resonator sensor comprising a surface to which a high recognition component is immobilized,
     the high recognition component being configured to selectively bind the analyte, an analyte molecule to which a tag is linked, or a tag, or any one of these molecules to which an amplification element-linked second recognition component is bound; and
   one or more containers housing an amplification molecule, the amplification element-linked second recognition component, and optionally one or both of the tag and the analyte molecule.

11. The kit of claim 10, wherein the amplification element comprises an enzyme and an amplification precursor comprising a substrate, and wherein the enzyme is configured to convert the substrate to a precipitate.

12. A method for detecting an analyte in a sample, comprising:
   contacting an analyte or an analyte and a tag-linked analyte molecule, a low recognition component, and an amplification element-linked second recognition component to generate a complex comprising the low recognition component and the amplification element-linked second recognition component,
     wherein the low recognition component is immobilized relative to a surface of a low sensitivity bulk acoustic wave (BAW) resonator sensor and is configured to selectively bind one or more of the analyte, the analyte molecule to which the tag is linked or the tag, or any one or more of these molecules bound to the second recognition component;
   contacting an analyte or an analyte and a tag-linked analyte molecule, a high recognition component, and an amplification element-linked second recognition component to generate a complex comprising the high recognition component and the amplification element-linked second recognition component,
     wherein the high recognition component is immobilized relative to a surface of a high sensitivity BAW resonator sensor and is configured to selectively bind one or more of the analyte, the analyte molecule to which the tag is linked or the tag, or any one or more of these molecules bound to the second recognition component;
     wherein the amplification element-linked second recognition component is configured to selectively bind the analyte, the analyte molecule to which the tag is linked or the tag, or any one or more of these molecules bound to the low and high recognition components;
     wherein the low recognition component and the high recognition component have different affinities for the analyte molecule;
   contacting the linked amplification element with an amplification precursor under conditions to convert the amplification precursor into a molecule that adds mass at a surface of the BAW resonator sensor; and
   measuring mass added at the surface of the BAW resonator sensor.

13. The method of claim 12, wherein the analyte or the analyte and the tag-linked analyte molecule are contacted with the amplification element-linked second recognition component prior to contact with both the low and high recognition components immobilized relative to the surface of the low and high sensitivity BAW resonator sensors, respectively.

14. The method of claim 13, wherein the analyte or the analyte and the tag-linked analyte molecule are contacted with the low and high recognition components prior to contact with the amplification element-linked second recognition component.

15. The method of claim 13, wherein the analyte or the tag-linked analyte molecule, the low recognition component, the high recognition component, and the amplification element-linked second recognition component are contacted simultaneously.

16. A method for detecting an analyte in a sample, comprising:
   contacting an analyte or an analyte and a tag-linked analyte molecule, a low recognition component, and an amplification element-linked second recognition component to generate a complex comprising the low recognition component and the amplification element-linked second recognition component,
     wherein the low recognition component is immobilized relative to a surface of a low sensitivity bulk acoustic wave (BAW) resonator sensor, is configured to selectively bind one or more of the analyte, the analyte molecule to which the tag is linked or the tag, or any one or more of these molecules bound to the second recognition component and has a low concentration on the surface to which it is immobilized;
   contacting an analyte or an analyte and a tag-linked analyte molecule, a high recognition component, and an amplification element-linked second recognition component to generate a complex comprising the high recognition component and the amplification element-linked second recognition component,
     wherein the high recognition component is immobilized relative to a surface of a high sensitivity BAW resonator sensor, is configured to selectively bind one or more of the analyte, the analyte molecule to which the tag is linked or the tag, or any one or more of these molecules bound to the second recognition component and has a high concentration on the surface to which it is immobilized;
     wherein the amplification element-linked second recognition component is configured to selectively bind the analyte, the analyte molecule to which the tag is linked or the tag, or any one or more of these molecules bound to the low and high recognition components;

wherein the low concentration of the low recognition component is lower than the high concentration of the high recognition component;

contacting the linked amplification element with an amplification precursor under conditions to convert the amplification precursor into a molecule that adds mass at a surface of the BAW resonator sensor; and measuring mass added at the surface of the BAW resonator.

17. The method of claim 16, wherein the surface of the low sensitivity BAW resonator sensor also has a non-specific component immobilized thereon.

18. The method of claim 16, wherein the low and high recognition components are the same.

* * * * *

UNITED STATES PATENT AND TRADEMARK OFFICE
CERTIFICATE OF CORRECTION

PATENT NO. : 11,408,855 B2
APPLICATION NO. : 16/503720
DATED : August 9, 2022
INVENTOR(S) : James Russell Webster and Ian Robert Harmon Page 1 of 1

It is certified that error appears in the above-identified patent and that said Letters Patent is hereby corrected as shown below:

In the Claims

At Column 12, Line 67, Claim 5: Please replace "sensitivity high sensitivity" with "high sensitivity".

Signed and Sealed this
Twenty-seventh Day of September, 2022

Katherine Kelly Vidal
*Director of the United States Patent and Trademark Office*